United States Patent [19]

Sturm

[11] 4,001,284
[45] Jan. 4, 1977

[54] PROCESS FOR THE MANUFACTURE OF 5-SULFAMOYL-ANTHRANILIC ACIDS
[75] Inventor: Karl Sturm, Heidesheim, Germany
[73] Assignee: Hoechst Aktiengesellschaft, Frankfurt am Main, Germany
[22] Filed: Feb. 12, 1975
[21] Appl. No.: 549,430
[30] Foreign Application Priority Data
Feb. 14, 1974  Germany .......................... 2406972
[52] U.S. Cl. ...................... 260/397.7 R; 260/239.6
[51] Int. Cl.² .............. C07C 143/78; C07C 143/80
[58] Field of Search ...................... 260/397.7, 239.6
[56] References Cited
UNITED STATES PATENTS
3,658,990  4/1972  Werner ........................... 260/397.7
3,793,311  2/1974  Feit et al. ....................... 260/397.7

OTHER PUBLICATIONS

J. of Chem. Soc., pp. 1168–1173 (1927), LeFevre et al., "The Scission of Diaryl Ethers and . . ., Piperdine."
"Mechanism and Structure in Org. Chemistry," Gould, Henry Holt & Co., New York, pp. 429 and 434 (1959).
J. Med. Chem. 15(1), 79–83 (1971), Feit et al., "Aminobenzoic Acid Diuretics . . . Derivatives.

Primary Examiner—Albert T. Meyers
Assistant Examiner—D. W. Robinson
Attorney, Agent, or Firm—Curtis, Morris & Safford

[57] ABSTRACT

A process for the manufacture of sulfamoyl anthranilic acids of the general formula I

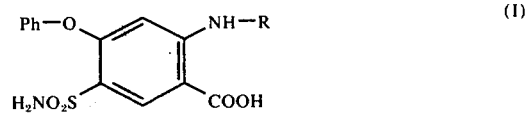

in which Ph is phenyl substituted with 1 or 2 halogen atoms, alkyl groups or etherified hydroxy groups, and R is aralkyl, heteroaralkyl or cycloalkyl-alkyl, unsaturated in the aliphatic moiety, including oxygen or sulfur and/or substituted with halogen, alkyl or alkoxy in the aromatic moiety, by reacting carboxylic acids with at least one mol-equivalent of an amine
(R—NH₂)
at a temperature above 120° C.

3 Claims, No Drawings

PROCESS FOR THE MANUFACTURE OF 5-SULFAMOYL-ANTHRANILIC ACIDS

The present invention relates to a process for the manufacture of 5-sulfamoylanthranilic acids of the general formula I

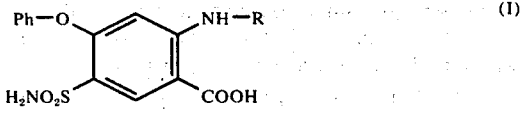

in which Ph stands for a phenyl radical which may carry 1 or 2 halogen atoms, alkyl groups or etherified hydroxy groups, and R stands for an aralkyl, hetero aralkyl or cycloalkyl-alkyl radical which may be unsaturated in the aliphatic moiety, or may include oxygen or sulfur and/or carry halogen atoms, alkyl or alkoxy radicals in the aromatic moiety.

The process of this invention comprises reacting a carboxylic acid of the general formula IV

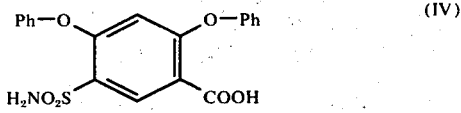

wherein Ph is defined as above, with at least one mol-equivalent of an amine of the general formula
R — NH$_2$
in which R is defined as above, at temperatures above 120° C.

The starting substances of formula IV may be prepared according to the following formula scheme:

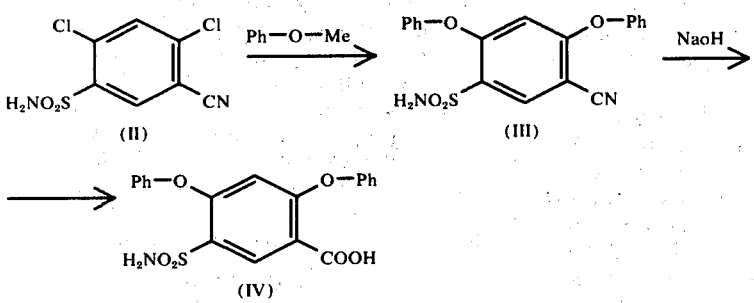

in which Ph is defined as above and Me is an alkali metal.

The 2,4-dichloro-5-sulfamoyl benzonitrile of formula II used as starting material for the first step was disclosed for the first time in Chemische Berichte, Vol. 99 (1966), page 350. In a manner which is simpler than indicated there, this compound can be prepared from 2,4-dichloro-5-sulfamoyl-benzoic acid, which is being produced nowadays on an industrial scale, by a reaction with thionyl chloride, subsequent reaction of the corresponding acid chloride with ammonia and conversion of the amide into the nitrile by means of phosphoroxy chloride.

2,4-dichloro-5-sulfamoyl-benzonitrile of formula II is then reacted with 2 equivalents of an alkali metal phenolate of the formula Ph-O-Me at temperatures of from 100° to 150° C. It is advantageous to use the sodium or potassium salts of these phenols and to carry out the reaction at a temperature of from 110° to 140° C. To keep the reaction mixture in a liquid state, it is advantageous to add, in addition to the 2 mol-equivalents of alkali metal phenolate required, an aprotic high-boiling solvent which should suitably be miscible with water, for example dimethylformamide, diethylformamide, dimethyl-sulfoxide, dimethylacetamide, tetramethylene-sulfone, tetramethyl-urea, diethylene glycol dimethyl ether or hexamethyl-phosphoric acid triamide.

Instead of one of these solvents, the corresponding phenol in the free form (PhOH) may also be employed as a solvent for the manufacture of the compound of formula III, in addition to the 2 mol-equivalents of Ph-O-Me required as a reaction component. This reaction variant is, however, only advantageous if the phenols are sufficiently soluble in water or readily volatile in steam and are easily obtainable.

The alkali metal phenolate may also be prepared in situ by adding 2 mol-equivalents of an alkali metal hydroxide, preferably sodium hydroxide, or a mol-equivalent of an alkali metal carbonate, to a mixture of 2,4-dichloro-5-sulfamoyl-benzonitrile and at least 2 equivalents of Ph-OH, advantageously in the presence of one of the aforesaid solvents, and then heating the mixture slowly, while stirring, to the required reaction temperature. Instead of the alkali metal hydroxides and carbonates, other acid-binding agents, such as for example magnesium oxide, calcium oxide or triethylamine, may generally also be used.

As reaction components of the general formula Ph-OH, there are mentioned, in addition to phenol, for example the following substituted phenols: isomeric mono- and dichloro-phenols, isomeric bromophenols, isomeric mono- and dimethyl-phenols, isomeric ethylphenols, isomeric mono- and dimethoxy-phenols, isomeric mono- and diethoxy-phenols, isomeric phenoxy- and benzyloxy-phenols, isomeric chloromethoxyphenols and isomeric chloromethyl- and methoxymethyl-phenols.

The hot liquid reaction mixture is advantageously worked up by introducing it into water, whereupon the bisphenoxy derivative formed generally precipitates in crystals. The precipitate is obtained in amorphous form whenever a phenol which is sparingly soluble in water has been used. In such a case, the precipitate is advantageously separated by decanting it and treating it with diethyl ether or a dilute sodium hydroxide solution.

If phenol is used in a large excess, it can also be separated by steam distillation.

The crude products of the general formula III are advantageously purified by recrystallization from methanol, ethanol, isopropanol, nitromethane or a mixture of ethyl acetate and petroleum ether.

The nitriles of the general formula III are then hydrolyzed to yield the corresponding carboxylic acids of formula IV. The hydrolysis reaction is advantageously carried out by heating an excess amount of an aqueous sodium or potassium hydroxide solution under reflux. After the initial suspension has passed into a clear solution within about 1 to 2 hours, further refluxing for about half an hour may be advantageous. When sparingly soluble nitriles of formula III are used, the reaction time may be shortened by adding ethanol or dioxan. Acidification of the alkaline reaction solution, optionally filtered, precipitates the carboxylic acids of formula IV almost quantitatively. For purification, the precipitate, which has been carefully washed with water, is advantageously recrystallized from a low-molecular-weight alcohol, preferably ethanol or isopropanol, or from dioxan. The yields obtained from this reaction step exceed 90 % of the theoretical yields.

According to the process of the invention, the carboxylic acids of formula IV are reacted with at least one mol-equivalent of an amine of the general formula R—NH$_2$; the products of the general formula I are obtained in a high yield by means of substitution of that phenoxy radical, which is in ortho-position to the carboxyl group. The reaction temperatures required for this reaction exceed 120° C and preferably range from 120° to 160° C, an advantageous temperature range being from 130° to 150° C, wherein, on the one hand, no appreciable side reactions take place and, on the other hand, the reaction is complete within a period of from 2 to 4 hours.

Particularly good yields are obtained from a reaction which is carried out without a solvent but with an excess amount of the base used. In many cases, 3 to 4 mol-equivalents of R—NH$_2$ are sufficient to keep the reaction mixture in liquid state. When easily obtainable amines are used, the excess amount may also be increased up to 10 mol-equivalents, since the reaction products of formula I are difficultly soluble in aqueous acids and therefore the excess base can be separated in simple manner. When bases are used which are available with difficulty, the excess base is advantageously reduced while adding an inert diluent miscible with water, for example glycol diethyl ether or diethyleneglycol dimethyl ether. The addition of an acid-binding agent, for example sodium hydroxide, potassium carbonate, pyridine or triethylamine, or the use of the carboxylic acids of formula IV in the form of their alkali metal or alkaline earth metal salts is likewise possible.

As reaction components of the general formula R—NH$_2$, there are mentioned, for example, the following amines: isomeric furyl-methyl and furyl-ethyl amines, isomeric thienylmethyl and thienyl-ethyl amines, benzylamine, isomeric phenylethyl and phenylpropyl amines, isomeric mono- and dichloro-benzyl amines, isomeric bromo-benzyl amines, isomeric mono- and dimethyl-benzyl amines, isomeric mono- and dimethoxy-benzyl amines, piperonyl amine, isomeric chloromethyl-, chloromethoxy- and methoxymethyl-benzyl amines, cinnamyl amine, 2-phenoxy- and 2-phenyl-thioethyl amine, cyclo-pentyl- and cyclopentenyl-methyl amine, cyclohexyl- and cyclo-hexenyl-methyl amine, cycloheptyl- and cyclooctyl-methyl amine, isomeric tetrahydro-furyl-methyl and pyranyl-methyl amines and isomeric pyridylmethyl amines.

For isolating the end products of formula I, the reaction mixture, optionally after dilution with methanol, ethanol or acetone, is advantageously introduced into dilute aqueous hydrochloric acid. If the radical R is unstable towards acids, for example a furylmethyl or thienylmethyl radical, it is advisable to introduce the reaction solution into dilute acetic acid and then to adjust the pH of the mixture to 3 by adding hydrochloric acid and cooling with ice. The end products of formula I are difficulty soluble in aqueous acids and precipitate in an almost quantitiative yield. In this final stage, the crude precipitate, which has been carefully washed with water, is suitably purified by recrystallizing it from a low-molecular-weight alcohol, nitromethane, dioxan, ethyl acetate, butyl acetate or a mixture of dimethylformamide with a low-molecular-weight alcohol. The final yields range from 70 to 90 % of the theoretical yields.

The products of the general formula I are already known from the Journal of Medicinal Chemistry, Vol. 15, pages 79 – 83 (1971) to be compounds with valuable diuretic properties.

The advantage of the process of this invention consists in it being far simpler and providing substantially higher yields than the process known in the art for preparing the compounds which latter process necessarily requires the use of scarcely available fluorobenzene derivatives for the manufacture of the starting substances.

The following table presents a comparison of yields of the known compounds Ia to Ic as examples.

TABLE

| | Prior art process | Process of this invention |
|---|---|---|
| Ia | 13 % of the theory | 81 % of the theory |
| Ib | 8 % of the theory | 74 % of the theory |
| Ic | 26 % of the theory | 86 % of the theory |

The smooth reaction according to the process of the invention is surprising. Although the nucleophilic substitution of a phenoxy radical linked to the dinitrophenyl ring by piperidine and pyridine has been disclosed in the art, such a substitution in a phenyl radical substituted by nitrilo or sulfamoyl groups has not been known yet. It could not be forseen which isomer would eventually be formed by the partial substitution of a phenoxy radical.

The following Examples illustrate the invention.

EXAMPLE 1

N-(2-furylmethyl)-4-phenoxy-5-sulfamoyl-anthranilic acid a. 2,4-dichloro-5-sulfamoyl-benzamide 2.7 kg (10 mols) of 2,4-dichloro-5-sulfamoyl-benzoic acid were refluxed for 2 hours with 1.4 kg of thionyl chloride and 3.0 l of dioxan. The reaction solution was then concentrated by evaporation in vacuo, the residue was taken up in 5 l of acetone and the acetone solution was introduced within half an hour, while stirring at room temperature, into 15 l of concentrated aqueous ammonia. The reaction mixture was then concentrated in vacuo to half its volume and 2,4-dichloro-5-sulfamoyl benzamide was precipitated with 10 l of water to yeild crystals. After suction-filtration and thorough washing with water, the product was dried on a steam bath.

Yield: 2.35 kg (87 % of the theoretical yield), m.p. 206° – 209° C.

b. 2,4-dichloro-5-sulfamoyl-benzonitrile 1.35 kg (5 mols) of this crude amide were rapidly heated to 90° 100° C while stirring with 2.0 l of phosphoroxy chloride. At this temperatutre, the reaction set in while the previously suspended amide went into solution with formation of hydrochloric acid. About 10 minutes later, the nitrile formed started crystallizing from the clear reaction solution. Stirring was continued for 15 minutes at 105° C, and then the hot reaction solution was introduced portionwise while stirring into 20 l of water that had been preheated to 30° C. The temperature was maintained between 30 and 35° C by adding ice. After this addition, the temperature was reduced to about 10° C, the 2,4-dichloro-5-sulfamoyl-benzonitrile precipitating in crystals was suction-filtered, washed with water until neutral and dried on a steam bath.

Yield: 1.15 kg (92 % of the theoretical yield), m.p. 196° – 197° C.

c. 2,4-diphenoxy-5-sulfamoyl-benzonitrile

A mixture of 251 g of 2,4-dichloro-5-sulfamoyl-benzonitrile (1.0 mol), 400 ml of dimethylformamide, 200 g of phenol and 80 g of sodium hydroxide was stirred for 3 hours at 130° C. The mixture was then allowed to cool to about 90° C and when its viscosity was low and it was turbid from precipitated NaCl, it was introduced into 10 l of water. After having been allowed to stand for 1 hour at room temperature, the light grey crystallized precipitate was suction-filtered, washed several times with water, and the product still moist after filtration was then recrystallized from isopropanol. The product was first dried in the air and then on a steam bath until its weight remained constant. The colorless crystals thus obtained still contained one mol-equivalent of isopropanol.

Yield: 230 g (54 % of the theoretical yield), m.p. 148°–150° C.

d. 2,4-diphenoxy-5-sulfamoyl-benzoic acid 43 g (0.1 mol) of the 2,4-diphenoxy-5-sulfamoyl-benzonitrile prepared according to (c) were heated while stirring with 0.8 l of 2N NaOH for 2 hours on a steam bath. 0.8 l of 2N HCl was then added while vigorously stirring to the clear solution which had been cooled to room temperature. After standing for a short time at room temperature, the crystallized precipitate was suction-filtered and the moist product, which had been washed with water, was recrystallized from ethanol. After drying on a steam bath, the compound still contained 1-mol-equivalent of ethanol.

Yield: 39 g (90 % of the theoretical yield), m.p.. 213° – 214° C.

e. N-(2-furylmethyl)-4-phenoxy-5-sulfamoyl-anthranilic acid (end product)

43 g (1.0 mol) of the 2,4-diphenoxy-5-sulfamoyl-benzoic acid prepared according to (d) were stirred for 4 hours under nitrogen at 135° C with 90 ml of freshly distilled furfurylamine. The faintly yellow reaction solution, which had been cooled to about 80° C, was then introduced while stirring into 1 l of 10 % acetic acid, and the pH of the mixture was then adjusted to 3 by means of 5N HCl. After standing for a short time at room temperature, the N-(2-furylmethyl)-4-phenoxy-5-sulfamoyl-anthranilic acid which had precipitated in crystals was suction-filtered, washed with water and ethanol and dried on a steam bath.

Yield: 31.6 g (81 % of the theoretical yield), decomposition point: 236° C.

After recrystallization from nitromethane, the decomposition point was 241° C.

EXAMPLE 2

N-benzyl-4-phenoxy-5-sulfamoyl-anthranilic acid

The reaction was the same as in Example 1 (e) using, however, 100 ml of benzylamine instead of 2-furylmethylamine. The yield of the crude product was 38 g (97 % of the theoretical yield), m.p. 237° – 239° C. Purification by recrystallization from ethanol.

Yield: 34.4 g (86 % of the theoretical yield), m.p. 244° – 246° C.

EXAMPLE 3

N-(2-thienylmethyl)-4-phenoxy-5-sulfamoyl-anthranilic acid

The reaction was carried out as in Example 1 (e) using a mixture of 50 ml of 2-thienylmethylamine and 30 ml of diethylene glycol dimethyl ether instead of 2-furylmethylamine and applying a reaction temperature of 140° C. The crude product was recrystallized from ethanol.

Yield: 30.6 g (74 % of the theoretical yield), decomposition point: 231° C.

EXAMPLE 4

N-(3-chlorobenzyl)-4-phenoxy-5-sulfamoyl-anthranilic acid

The reaction was carried out as in Example 1 (e) using 100 ml of 3-chlorobenzylamine instead of 2-furfurylamine within a reaction time of 5 hours at 140° C. The crude product which had precipitated in crystals was recrystallized twice from ethanol.

Yield: 32.6 g (75 % of the theoretical yield), decomposition point: 256° C.

EXAMPLE 5

N-(4-pyridylmethyl)-4-phenoxy-5-sulfamoyl-anthranilic acid

The reaction was carried out as in Example 1 e using, instead of 2-furfurylamine, 100 ml of pyridylmethylamine within a reaction time of 4 hours. The yellow reaction solution was introduced into 1 l of water. By-products which had precipitated in an amorphous form were separated, and the light yellow solution was acidified with dilute HCl to reach a pH of 5. The end product, which had first precipitated in an amorphous form, crystallized upon standing overnight at room temperature. It was suction-filtered and freed from byproducts by boiling it with ethanol, in which it was sparingly soluble.

Yield: 25.2 g of yellow crystals (63 % of the theoretical yield), decomposition point: 254° C.

EXAMPLE 6

N-(2-methoxybenzyl)-4-phenoxy-5-sulfamoyl-anthranilic acid 43 g of 2,4-diphenoxy-5-sulfamoyl-benzoic acid (0.1 mol) prepared according to Example 1 (c) were stirred with 80 ml of 2-methoxybenzylamine for 3.5 hours at 140° C. The almost colorless reaction solution which, had been cooled to about 80° C, was then diluted with 150 ml of ethanol, and the solution was introduced while stirring into 1.0 l of 1N hydrochloric acid at room temperature. The reaction product, which had precipitated in crystals, was suction-filtered and washed with water and then boiled up for a short time with 0.3 l of ethanol, during which the major part of it remained undissolved. After cooling to room temperature, it was suction-filtered and washed with ethanol and finally dried on a steam bath.

Yield: 32.4 g (74 % of the theoretical yield), decomposition point: 254° C.

EXAMPLE 7

N-(2-tetrahydrofurylmethyl)-4-phenoxy-5-sulfamoyl-anthranilic acid

The reaction was carried out as in Example 6 using 80 ml of 2-tetrahydrofurylmethylamine instead of 2-methoxybenzylamine. The amorphous crude product was recrystallized from ethanol/water.

Yield: 31.0 g (79 % of the theoretical yield), decomposition point: 210° – 211° C.

EXAMPLE 8

N-cyclohexylmethyl-4-phenoxy-5-sulfamoyl-anthranilic acid

The reaction was carried out as in Example 6 using 100 ml of cyclohexylmethylamine instead of 2-methoxybenzylamine. The crystallized crude product was recrystallized from ethanol.

Yield: 36.8 g (66 % of the theoretical yield), decomposition starting from 220° C.

EXAMPLE 9

N-(2-furylmethyl)-4-(3-chlorophenoxy)-5-sulfamoyl-anthranilic acid a. 2,4-di-(3-chlorophenoxy)-5-sulfamoyl-benzonitrile The reaction was carried out as in Example 1 (c) using 260 g of 3-chlorophenol instead of phenol. The reaction product, which had been first precipitated with water in an amorphous form, crystallized upon digesting with a mixture of isopropanol and water (about 1 : 10). Final-stage purification by recrystallization from methanol. Drying at 100° C under a pressure of 2 mm Hg.

Yield: 205 g (47 % of the theoretical yield), m.p. 146°–147° C.

b. 2,4-di-(3-chlorophenoxy)-5-sulfamoyl-benzoic acid 44 g (0.1 mol) of the nitrile prepared in (a) were refluxed with 0.5 l of 2N NaOH. After about 15 minutes, a clear solution was obtained. Refluxing was continued for one hour. After cooling to room temperature and acidification with 5N HCl, carboxylic acid precipitated at once in crystals. The moist product, which had been washed with water, was recrystallized from methanol.

Yield: 41 g (90 % of the theoretical yield), m.p. 202° – 204° C.

c. End product 45.5 g (0.1 mol) of the carboxylic acid prepared in (b) were stirred under nitrogen at 140° C for 4 hours with 100 ml of freshly distilled furfurylamine. The reaction solution, which had been cooled to 60° C and diluted with 100 ml of ethanol, was stirred into 1 l of 1N hydrochloric acid. The crystallized precipitate was separated, washed with water and recrystallized from ethanol. The crystals were dried at 100° C.

Yield: 32 g (76 % of the theoretical yield), decomposition point: 240° C.

EXAMPLE 10

N-(2-furylmethyl)-4-(4-methylphenoxy)-5-sulfamoyl-anthranilic acid a. 2,4-di-(4-methylphenoxy)-5-sulfamoyl-benzonitrile The reaction was carried out as in Example 1 (c) using 220 g of p-cresol instead of phenol. The crude product which first precipitated in an amorphous form was recrystallized from methanol and dried at 100° C under a pressure of 1 mmHg.

Yield: 185 g (47 % of the theoretical yield), m.p. 155° – 156° C.

b. 2,4-di-(4-methylphenoxy)-5-sulfamoyl-benzoic acid 39.5 g (0.1 mol) of the nitrile prepared in (a) were hydrolyzed with sodium hydroxide solution as in Example 9 (b). The crude product was purified by recrystallization from methanol.

Yield: 34 g (82 % of the theoretical yield), m.p. 238° – 239° C.

c. End product 41.5 g of the carboxylic acid prepared sub (b) (0.1 mol) were reacted with furfurylamine as in Example 9 (c), and the amorphous crude product was recrystallized from 50 % ethanol and dried at 100° C.

Yield: 29 g (72 % of the theoretical yield), decomposition point: 221° C.

EXAMPLE 11

N-benzylamino-4-(3-chlorophenoxy)-5-sulfamoyl-anthranilic acid 45.5 g of the carboxylic acid prepared in Example 9 (b) (0.1 mol) were reacted with 100 ml of benzylamine as in Example 9 (c), and the reaction product was purified by recrystallization from ethanol.

Yield: 38 g (88 % of the theoretical yield), decomposition point: 246° – 247° C.

EXAMPLE 12

N-(2-furylmethyl)-4-(4-methoxyphenoxy)-5-sulfamoylanthranilic acid a. 2,4-di-(4-methoxyphenoxy)-5-sulfamoyl-benzonitrile The reaction was carried out as in Example 1 (c) using 250 g of 4-hydroxy-anisole instead of phenol.

Yield: 190 g (44 % of the theoretical yield), m.p. 164° – 166° C.

b. 2,4-di-(4-methoxyphenoxy)-5-sulfamoyl-benzoic acid

The nitrile prepared according to (a) was hydrolyzed with 2N NaOH as in Example 9 (b). After recrystallization from ethanol, the carboxylic acid had a melting point of 246° – 248° C.

c. End product 44.6 g of the carboxylic acid prepared sub (b) were reacted with furfurylamine as in Example 9 (c). Upon recrystallization from ethanol, the product was dried at 100° C.

Yield: 34 g (81 % of the theoretical yield), decomposition Point: 216° C.

I claim:

1. A method of preferentially preparing a 5-sulfamoylanthranilic acid of the formula

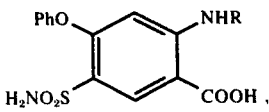

in a yield of 70–90 percent, where in Ph is phenyl or phenyl mono- or di-substituted with a member selected from the group consisting of halogen, lower alkyl, and lower alkoxy, and R is furylmethyl, thienylmethyl, pyridylmethyl, benzyl, benzyl mono- or di-substituted by halogen, lower alkyl, or lower alkoxy, or is cycloalkylmethyl having from 5 to 8 carbon atoms in the ring or heterocyclooxyalkyl methyl having from 4 to 5 carbon atoms in the ring, which method comprises reacting a 5-sulfamoylcarboxylic acid of the formula

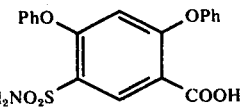

at a temperature between 120° and 160° C., with from 1 to 10 molar equivalents of an amine of the formula $RNH_2$.

2. A method as in claim 1 wherein said reaction is performed in the additional presence of an inert water-miscible organic solvent.

3. A method as in claim 2 wherein said organic solvent is glycol diethyl ether or diethylene glycol dimethyl ether.

* * * * *